US00PP31461P2

(12) United States Plant Patent
van Langen

(10) Patent No.: US PP31,461 P2
(45) Date of Patent: Feb. 18, 2020

(54) ***ECHEVERIA* PLANT NAMED 'TSAECH1825'**

(50) Latin Name: ***Echeveria* hybrid**
Varietal Denomination: TSAECH1825

(71) Applicant: Tosjami B.V., Heerhugowaard (NL)

(72) Inventor: Gerard van Langen, Heerhugowaard (NL)

(73) Assignee: Tosjami B.V., Heerhugowaard (NL)

( * ) Notice: Subject to any disclaimer, the term of this patent is extended or adjusted under 35 U.S.C. 154(b) by 0 days.

(21) Appl. No.: 16/501,061

(22) Filed: Feb. 14, 2019

(51) Int. Cl.
*A01H 5/12* (2018.01)
*A01H 6/32* (2018.01)

(52) U.S. Cl.
USPC ..... Plt./373
CPC ..... *A01H 6/32* (2018.05); *A01H 5/12* (2013.01)

(58) Field of Classification Search
USPC ..... Plt./373
CPC ..... A01H 5/12
See application file for complete search history.

*Primary Examiner* — Kent L Bell
(74) *Attorney, Agent, or Firm* — Samuel R. McCoy, Jr.

(57) ABSTRACT

A new and distinct *Echeveria* plant named 'TSAECH1825' which is characterized by an abundance of thin succulent foliage growing in a basal rosette and eventually producing secondary rosettes born on short stems, moderately to heavily glaucous foliage with a general pale blue-green coloration which becomes suffused with pale red-purple when exposed to high levels ultraviolet light, foliage which is distally margined and tipped pale pink margins, and the stability of these characteristics from generation to generation.

4 Drawing Sheets

Latin name of the genus and species: The Latin name of the genus and species of the novel variety disclosed herein is *Echeveria* hybrid.

Variety denomination: The inventive variety of *Echeveria* disclosed herein has been given the variety denomination 'TSAECH1825'.

BACKGROUND OF THE INVENTION

Parentage: 'TSAECH1825' is a seedling selection resulting from the controlled pollination of an unnamed and unpatented *Echeveria lilacina* plant, the seed parent, with an unnamed and unpatented *Echeveria peacockii* plant, the pollen parent. The crossing was made by the inventor in the spring of 2014 at a commercial greenhouse in Heerhugowaard, the Netherlands. In the summer of 2015, one seedling resulting from the cross of 2014 was observed to exhibit unique growth and foliage characteristics and was isolated for further evaluation in order to confirm the distinctness and stability of the characteristics first observed. Upon confirmation of distinctness and stability, 'TSAECH1825' was selected for commercialization.

Asexual Reproduction: Asexual reproduction of the new cultivar 'TSAECH1825', by way of rooting leaf cuttings, was first initiated in the spring of 2016 at the inventor's commercial greenhouse in Heerhugowaard, the Netherlands. Through six subsequent generations, the unique features of this cultivar have proven to be stable and true to type.

SUMMARY OF THE INVENTION

The cultivar 'TSAECH1825' has not been observed under all possible environmental conditions. The phenotype may vary somewhat with variations in environment such as temperature, day length, and light intensity, without, however, any variance in genotype. The following traits have been repeatedly observed and are determined to be the unique characteristics of 'TSAECH1825'. These characteristics in combination distinguish 'TSAECH1825' as a new and distinct *Echeveria* cultivar:

1. 'TSAECH1825' exhibits an abundance of succulent foliage growing in a basal rosette, eventually producing secondary rosettes born on short stems; and
2. 'TSAECH1825' exhibits thin, spatulate to obovate shaped foliage with a conspicuous apiculate apex; and
3. 'TSAECH1825' exhibits moderately to heavily glaucous foliage with a general pale blue-green coloration, which is distally margined and tipped pale pink; and
4. 'TSAECH182' exhibits foliage which becomes suffused with pale red-purple when exposed to high levels ultraviolet light.

BOTANICAL DESCRIPTION OF THE PLANT

Figure 1:
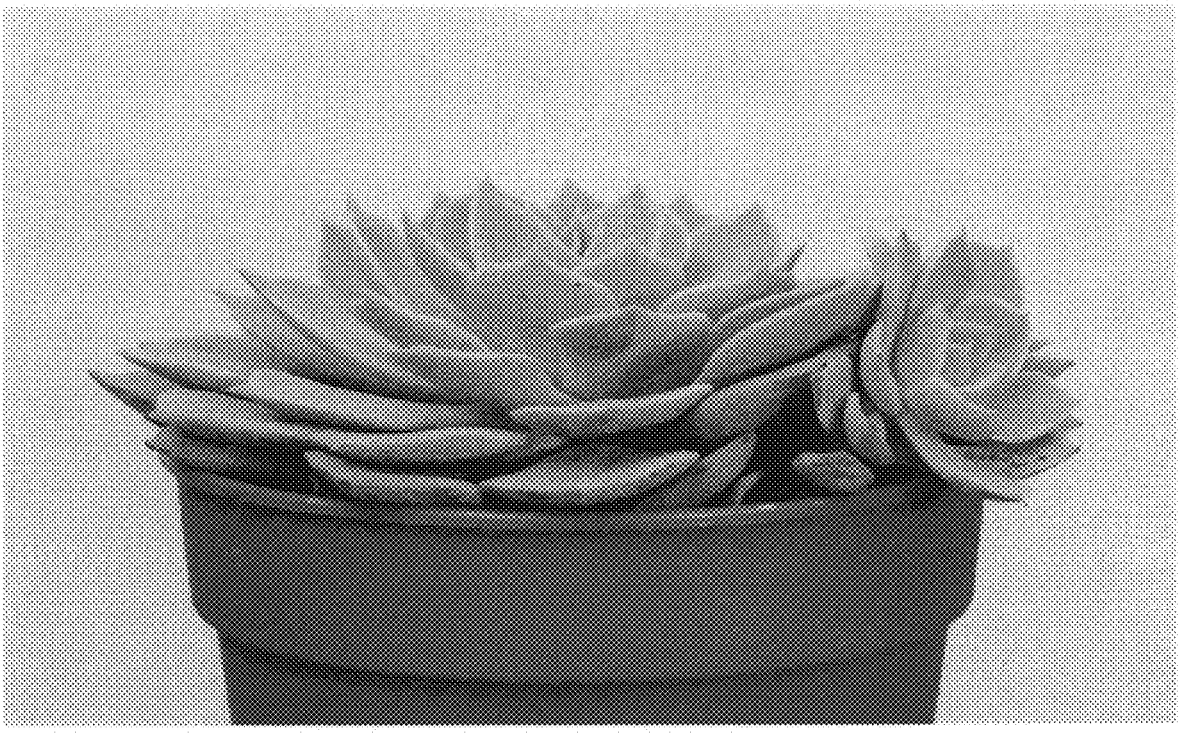
FIG. 1 illustrates, as nearly true as it is reasonably possible to make the same in color photographs of this type, an exemplary plant of 'TSAECH1825' grown in a commercial greenhouse in Heerhugowaard, the Netherlands. This plant is approximately 12 months old, shown planted in a 12 cm container.
Figure 2:
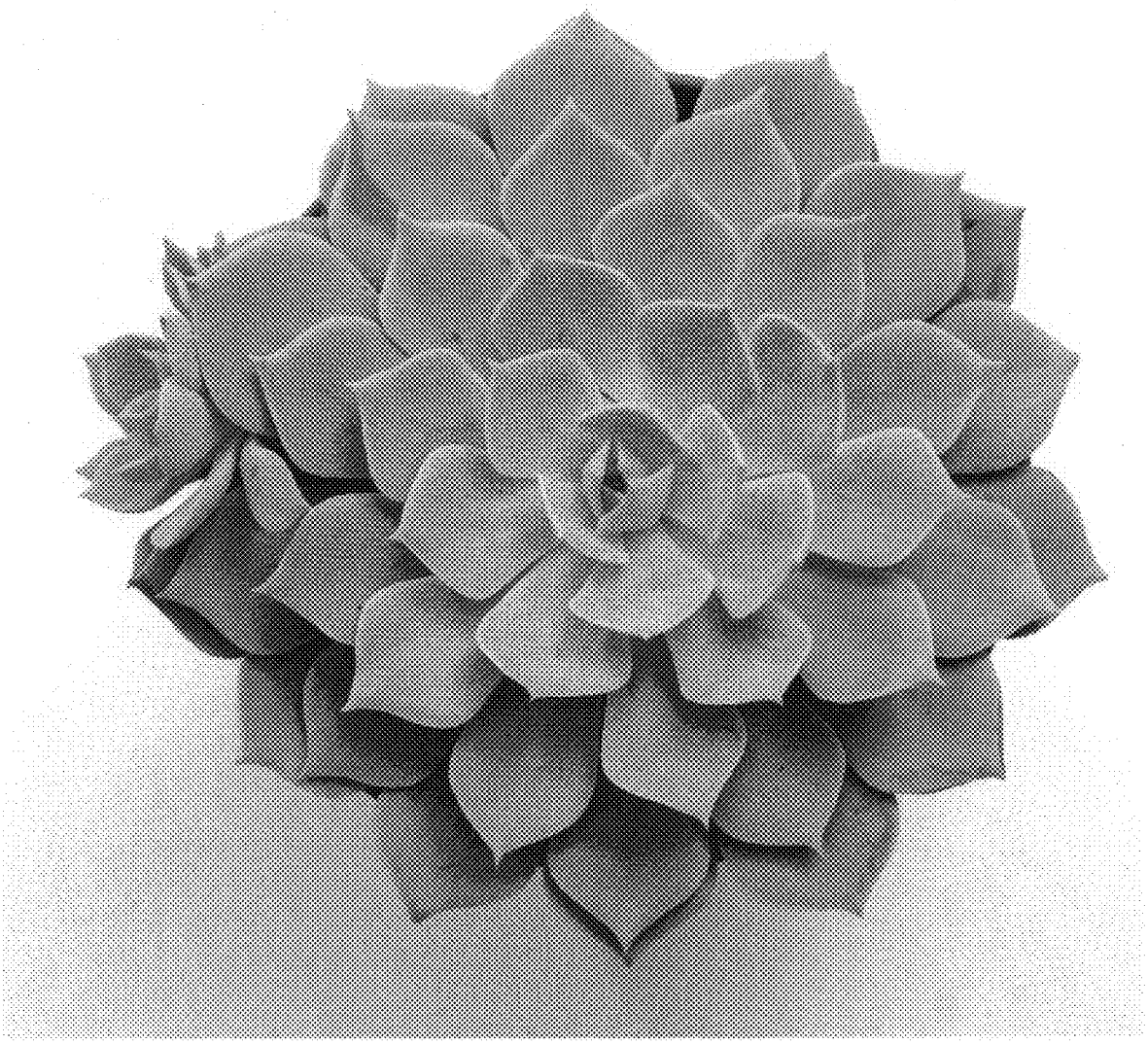
FIG. 2 illustrates, as nearly true as it is reasonably possible to make the same in color photographs of this type, the typical foliage arrangement of 'TSAECH1825'.
Figure 3:
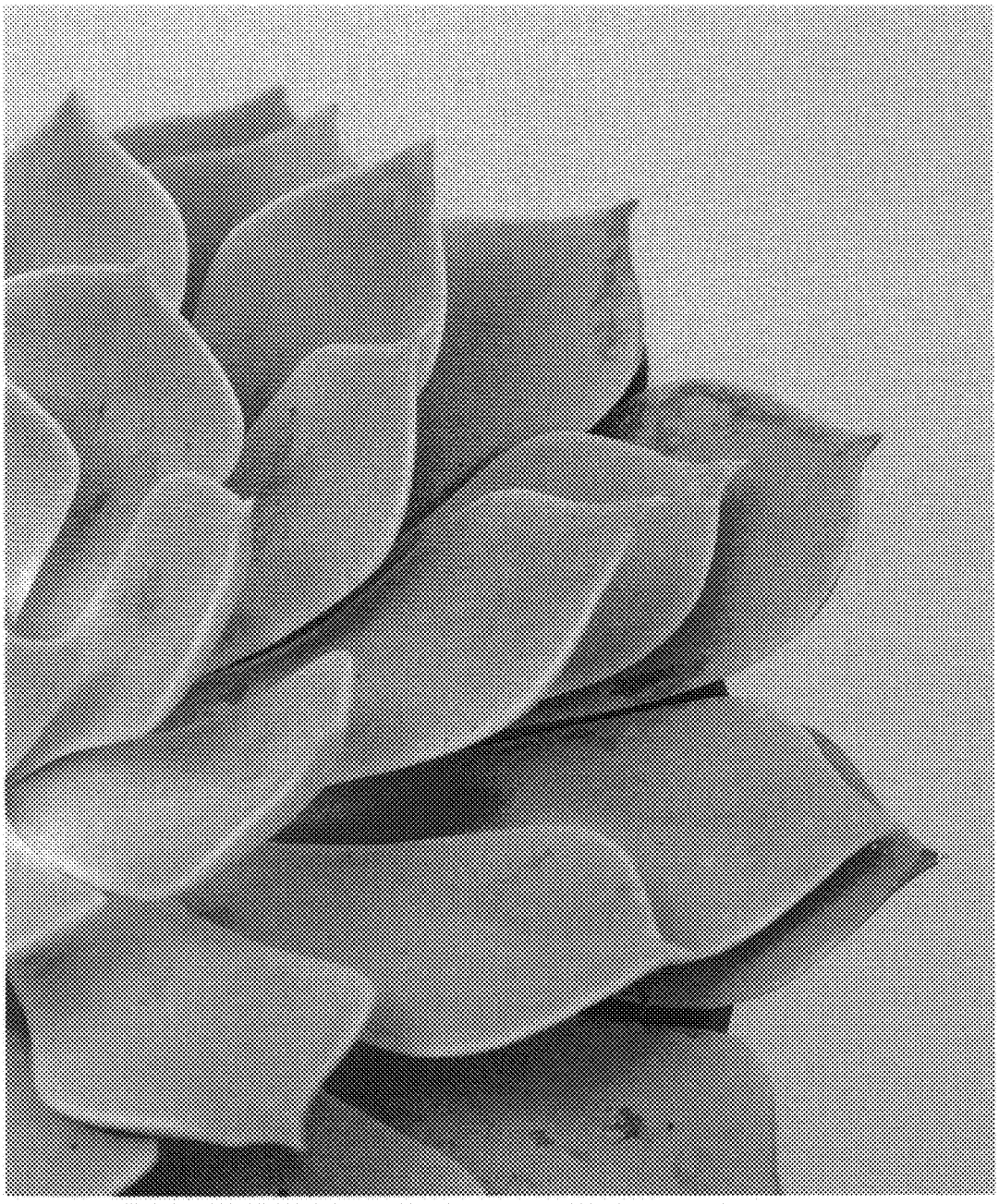
FIG. 3 illustrates, as nearly true as it is reasonably possible to make the same in color photographs of this type, the adaxial surface of the juvenile and mature foliage of 'TSAECH1825'.
Figure 4:
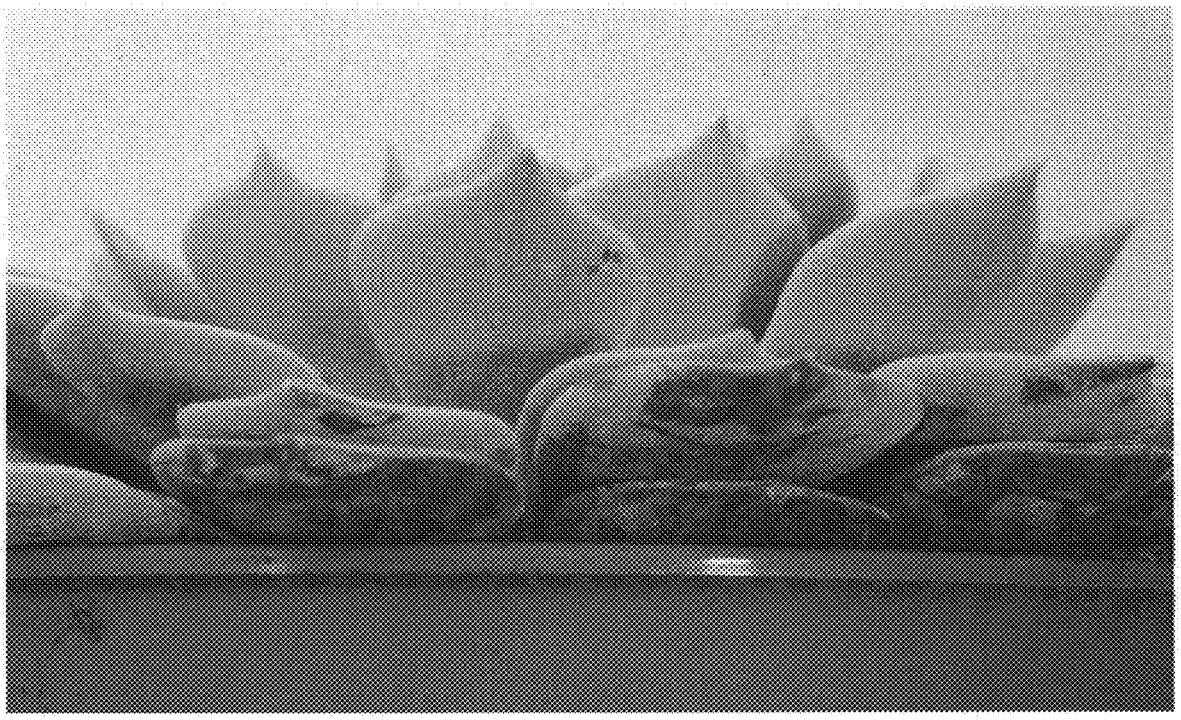
FIG. 4 illustrates, as nearly true as it is reasonably possible to make the same in color photographs of this type, the abaxial surface of the mature foliage of 'TSAECH1825'.

The following observations and measurements made in December of 2018 describe averages from a sample set of six specimens of 12 months old 'TSAECH1825' plants grown in 12 cm nursery containers at commercial greenhouse in Heerhugowaard, the Netherlands. Plants were produced using conventional greenhouse production protocols for *Echeveria* plants which consisted of minimal irrigation and fertilizer applications, and chemical pest and disease control measures against mealy bug and *Botrytis* as required. Plants were grown under approximately 50 percent shade after propagation and later exposed to full sun once they began to mature. No photoperiodic treatments or artificial light was given to the plants.

Those skilled in the art will appreciate that certain characteristics will vary with older or, conversely, with younger plants. 'TSAECH1825' has not been observed under all possible environmental conditions. Where dimensions, sizes, colors and other characteristics are given, it is to be understood that such characteristics are approximations or averages set forth as accurately as practicable. The phenotype of the variety may differ from the descriptions set forth herein with variations in environmental, climatic and cultural conditions. Color notations are based on *The Royal Horticultural Society Colour Chart*, The Royal Horticultural Society, London, 2015 (sixth edition).

A botanical description of 'TSAECH1825' and comparisons with the parent plants and closest known comparator are provided below.

Plant description:

*Growth habit*.—Succulent perennial with foliage growing in a basal rosette, eventually producing secondary rosettes born on short stems.

*Plant shape*.—Flattened.

*Height from soil level to top of foliar plane*.—4.8 cm.

*Plant spread*.—Average of 14.5 cm.

*Growth rate*.—Moderately fast growing.

*Plant vigor*.—Moderately vigorous.

*Propagation*.—Type — Leaf cuttings. Time to initiate rooting — Approximately 21 days at 18 degrees Celsius. Crop time — Approximately 25 weeks to produce a marketable plant in a 10.5 cm container.

*Disease and pest resistance or susceptibility*.—Neither resistance nor susceptibility to typical *Echeveria* pests and diseases has been observed.

*Environmental tolerances*.—Adapt to, at least, USDA Zones 10 to 12 and temperatures as high as 40 degrees Celsius; moderate tolerance to rain yet drought tolerant once established; high tolerance to wind.

Root system:

*General*.—Fine, well-branched fibrous roots.

Stems:

*Branching habit*.—Leaves in a basal rosettes, with lateral branches growing from the base.

*Quantity of lateral branches*.—1, as observed.

*Dimensions*.—5.6 cm long and 0.5 cm in diameter.

*Internode length*.—0.6 cm.

*Aspect*.—Rounded.

*Attitude*.—Nearly horizontal.

*Strength*.—Moderately strong.

*Texture and luster*.—Glabrous and matte; moderately glaucous.

*Color when developing*.—Yellow-green, nearest to RHS 146D; epicuticular wax covering the stem is nearest to a mixture of blue-green and greyed-green, RHS 122D and 189D.

*Mature color*.—Yellow-green, nearest to RHS 146D epicuticular wax covering the stem is nearest to a mixture of blue-green and greyed-green, RHS 122D and 189D.

*Color at internodes*.—Yellow-green, nearest to RHS 146D epicuticular wax covering the stem is nearest to a mixture of blue-green and greyed-green, RHS 122D and 189D.

Foliage:

*Arrangement*.—Rosette.

*Division*.—Simple.

*Attachment*.—Sessile.

*Quantity*.—Approximately 58 leaves per rosette.

*Shape*.—Spatulate to obovate.

*Dimensions*.—6.1 cm long, 2.7 cm wide, and 0.5 cm thick, on average.

*Aspect*.—Slightly concave and slightly curved upwards.

*Attitude*.—Juvenile foliage at the center of the rosette is held outward; foliage becomes progressively more relaxed towards the outer whorls of mature foliage, to near horizontal.

*Apex*.—Apiculate.

*Base*.—Long cuneate.

*Margin*.—Entire; not undulated.

*Pubescence, texture and luster of the adaxial surface*.—Glabrous, smooth, and matte; heavily glaucous.

*Pubescence, texture and luster of the abaxial surface*.—Glabrous, smooth, and matte; moderately to heavily glaucous.

*Color*.—Juvenile foliage, adaxial surface — Nearest to in between green and greyed-green, RHS 138A and 191A, and fading to a lighter shade of greyed-green towards the base, nearest to RHS 193B; margined yellow-green, nearest to RHS N148D; the epicuticular wax covering the leaf surface is nearest to a mixture of blue-green and greyed-green, RHS 122C and 188A, with more blue-green than greyed-green present. Juvenile foliage, abaxial surface — Green, nearest to RHS 138B, and fading to a light greyed-green towards the base, nearest to RHS 193B; margined yellow-green, nearest to RHS N148D; the epicuticular wax covering the leaf surface is nearest to a mixture of blue-green and greyed-green, RHS 122C and 188A, with more blue-green than greyed-green present. Mature foliage, adaxial surface — Yellow-green, nearest to RHS 148A, and fading to in between a lighter shade of yellow-green and greyed-green towards the base, nearest to RHS 148D and 193A; margined yellow-green, nearest to RHS 152D; the epicuticular wax covering the leaf surface is nearest to a mixture of blue-green and greyed-green, RHS 122C and 188A, with more blue-green than greyed-green present. Mature foliage, abaxial surface — Yellow-green, nearest to in between RHS 148A and 148B, and fading to in between a lighter shade of yellow-green and greyed-green towards the base, nearest to RHS 148D and 193A; margined yellow-green, nearest to RHS 152D; distally suffused with greyed-orange, nearest to RHS 164B; the epicuticular wax covering the leaf surface is nearest to a mixture of blue-green and greyed-green, RHS 122C and 188A, with more blue-green than greyed-green present.

*Venation*.—No venation is visible.

*Petiole*.—No petiole; leaves are sessile.

Inflorescence: No flowering has been observed to date.

COMPARISONS WITH THE PARENT PLANT AND CLOSEST KNOWN COMPARATOR

Plants of the new cultivar 'TSAECH1825' differ from the seed parent, an unnamed *Echeveria lilacina* plant (not patented), in the following characteristics described in Table 1 below.

TABLE 1

| Characteristic | 'TSAECH1825' | Seed parent |
|---|---|---|
| Foliage thickness. | Thinner than the seed parent. | Thicker than 'TSAECH1825'. |
| Foliage width. | Narrower than the seed parent. | Broader than 'TSAECH1825'. |
| General coloration of the foliage. | A mixture of blue-green to greyed, darker than the seed parent, and generally appearing as light blue-green. | A mixture of blue-green to greyed, lighter than 'TSAECH1825', and generally appearing as pale grey. |

Plants of the new cultivar 'TSAECH1825' differ from the pollen parent, an unnamed *Echeveria peacockii* plant (not patented), in the following characteristics described in Table 2 below.

TABLE 2

| Characteristic | 'TSAECH1825' | Pollen parent |
|---|---|---|
| Foliage thickness. | Thinner than the seed parent. | Thicker than 'TSAECH1825'. |

TABLE 2-continued

| Characteristic | 'TSAECH1825' | Pollen parent |
|---|---|---|
| General coloration of the foliage. | A mixture of blue-green to greyed, lighter than the pollen parent, and generally appearing as light blue-green. | A mixture of blue-green to greyed, lighter than the pollen parent, and generally appearing as light blue-grey. |

COMPARISONS WITH THE CLOSEST KNOWN COMPARATOR

Plants of the new cultivar 'TSAECH1825' differ from the closest known commercial comparator, *Echeveria* sp. 'Canadian' (not patented), in the following characteristics described in Table 3 below.

TABLE 3

| Characteristic | 'TSAECH1825' | 'Canadian' |
|---|---|---|
| Foliage thickness. | Thinner than the seed parent. | Thicker than 'TSAECH1825'. |
| General coloration of the foliage. | A mixture of blue-green to greyed, and generally appearing as light blue-green. | A mixture of blue-green to greyed, lighter than the pollen parent, and generally appearing as light blue-grey. |

That which is claimed is:

1. A new and distinct variety of *Echeveria* plant named 'TSAECH1825', substantially as described and illustrated herein.

* * * * *